United States Patent [19]

Courty et al.

[11] Patent Number: 4,533,650

[45] Date of Patent: Aug. 6, 1985

[54] PROCESS FOR MANUFACTURING A CATALYST CONTAINING IRON, CHROMIUM AND POTASSIUM OXIDES AND AT LEAST ONE RARE EARTH METAL OXIDE, FOR USE IN DEHYDROGENATION REACTIONS

[75] Inventors: Philippe Courty, Houilles; Michel Roussel, Antony; Serge Leporq, Mantes la Ville; Jean-Francois Le Page, Rueil Malmaison; Philippe Varin, Massy, all of France

[73] Assignee: Institut Francais du Petrole, Rueil-Malmaison, France

[21] Appl. No.: 561,374

[22] Filed: Dec. 14, 1983

[30] Foreign Application Priority Data

Dec. 14, 1982 [FR] France ................................ 82 21085
Dec. 14, 1982 [FR] France ................................ 82 21086

[51] Int. Cl.$^3$ ......................... B01J 21/16; B01J 23/10
[52] U.S. Cl. ........................................ 502/84; 502/303
[58] Field of Search ................ 502/63, 84, 525, 303

[56] References Cited

U.S. PATENT DOCUMENTS

| | | | |
|---|---|---|---|
| 3,595,809 | 7/1971 | Kehl ........................................ | 502/303 |
| 3,897,367 | 7/1975 | Lauder ............................. | 502/525 X |
| 4,134,858 | 1/1979 | Courty ................................... | 502/63 |
| 4,152,300 | 5/1979 | Riesser ............................... | 502/302 |

*Primary Examiner*—Carl F. Dees
*Attorney, Agent, or Firm*—Millen & White

[57] ABSTRACT

A process for manufacturing catalysts containing, as oxides, iron, chromium, potassium, as well as a rare earth metal in a proportion, calculated in oxide weight, of 1–15% with respect to the final catalyst, comprises:

a first step, wherein a product is prepared by a reaction between compounds of rare earth metal(s) and of another metal selected from Fe, Cr, Co, Al or V, and a calcination; and a second step wherein a mixture is formed between the product resulting from the first step, the other necessary reactants and water; the resulting paste is dried after optional shaping and calcined. A clayish material can be used in the step.

The catalysts obtained present an improved efficiency in dehydrogenation reactions, particularly of ethylbenzene to styrene.

20 Claims, No Drawings

PROCESS FOR MANUFACTURING A CATALYST CONTAINING IRON, CHROMIUM AND POTASSIUM OXIDES AND AT LEAST ONE RARE EARTH METAL OXIDE, FOR USE IN DEHYDROGENATION REACTIONS

BACKGROUND OF THE INVENTION

The present invention relates to a process for manufacturing catalysts for use in dehydrogenation reactions and, particularly, in the dehydrogenation of saturated or monoethylenic aliphatic hydrocarbons of low molecular weight (containing, for example, from 2 to 8 carbon atoms) as well as in the dehydrogenation of alkylaromatic hydrocarbons (such as ethylbenzene or diethylbenzenes) to vinyl aromatic hydrocarbons (such as styrene or divinylbenzene). It also relates to the catalysts obtained by this process and their use in dehydrogenation reactions.

It is known that, in the dehydrogenation of the above-mentioned hydrocarbons, the hydrocarbon is passed, preferably with an additional high proportion of steam (1 to 30 moles H$_2$O/mole hydrocaron), over a catalyst at an hourly rate by volume, expressed in relation with the liquid hydrocarbon, from 0.05 to 5, preferably from 0.1 to 1 volume (STP) per volume of catalyst and per hour and at a temperature of about 450° to 750° C.

Prior art catalysts have been described for dehydrogenating olefinic hydrocarbons, such as butenes (to butadiene) or alkylaromatic hydrocarbons, such as ethylbenzene (to styrene), these catalysts containing a major proportion by weight of iron oxide, a potassium compound (oxide or carbonate), vanadium oxide, optionally chromium oxide, as well as small proportion (from 0.01 to 10% by weight) of at least one additional oxide of a metal such as aluminium, cadmium, copper, magnesium, manganese, nickel, rare earth metals, uranium and zinc. Such catalysts are described in particular in the French Pat. No. 2,387,200 which substantially corresponds to the U.S. Pat. Nos. 4,143,083 and 4,152,300. In these patents, the rare earth metals are defined as being the metals of atomic number from 58 to 71 included, i.e. from cerium to lutetium. The rear earth metals used in the examples are cerium, praseodymium and neodymium.

As a general rule, the catalysts are prepared by admixing in suitable proportions compounds of the metals included in their composition. This operation consists more particularly of a malaxing in the presence of water, so as to form a paste which is then optionally shaped (for example by extrusion), dried and thermally activated.

The French Pat. No. 2,270,003, which corresponds substantially to the U.S. Pat. No. 4,134,858, discloses the use of a clayish material in the manufacture of a dehydrogenation catalyst, mainly based on iron, chromium and potassium oxides. During the thermal activation, at a convenient temperature, generally between 850° and 1100° C., the clayish material combines with potassium oxide to form a double aluminium and potassium silicate (more particularly kaliophyllite). This technique makes it possible in particular to decrease the filling density of the catalyst.

It has now been discovered that is was possible to improve the catalytic properties of catalysts containing, as oxides, iron, chromium and potassium, as well as a rare earth metal, by a two-phase process which will be described hereinafter.

SUMMARY

This invention has thus for an object a process for manufacturing catalysts which contain, as oxides, iron, chromium, potassium, in particular in the following ratios by weight:

$\dfrac{Fe_2O_3}{K_2O}$ : from 1/1 to 10/1, preferably from 2/1 to 7/1;

$\dfrac{CrO_3}{K_2O}$ : from 0.05/1 to 0.4/1, preferably from 0.1/1 to 0.3/1 and $\dfrac{Fe_2O_3}{CrO_3}$ : from 15/1 to 40/1, preferably from 25/1 to 35/1;

optionally a double aluminium and potassium silicate whose composition is more particularly Al$_2$O$_3$, 2 SiO$_2$, K$_2$O (kaliophyllite), in a proportion of 5 to 40% by weight; and a rare earth metal in a proportion, calculated as oxide, of 1 to 15% by weight, preferably from 3 to 10% by weight.

When the catalyst contains a double aluminium and potassium silicate, it contains an excess of potassium oxide with respect to the amount combined as double silicate.

In this case, the potassium excess, calculated as oxide, is advantageously in the following proportions by weight with respect to iron oxide and chromium oxide:

$\dfrac{Fe_2O_3}{K_2O \text{ excess}}$ : from 3/1 to 10/1; and $\dfrac{CrO_3}{K_2O \text{ excess}}$ : from 0.1/1 to 0.4/1

Rare earth means, according to the invention, the elements from group III B of the periodic classification and, more particularly, scandium, yttrium and the lanthanides, whose atomic number ranges from 57 to 71 included.

As a general rule, the process for preparing the catalysts according to the invention, comprises:

A first step during which a product is prepared by reaction, of at least one compound of a rare earth metal (RE) with at least one compound of at least one metal (M) selected from iron, chromium, cobalt, aluminium and vanadium, said reaction being followed with heating at high temperature; and A second step, during which is effected a mixture comprising water, at least one iron compound, at least one chromium compound, at least one potassium compound and the product resulting from the first step, the various metal compounds being used in proportions corresponding to the indicated oxide proportions by weight, said mixture being malaxed to form a paste which is then dried and the catalyst being thermally activated by heating at high temperature.

In the first step of the process according to the invention, the metal compounds may be used in proportions corresponding to atomic ratios of the rare earth metal (RE) to the associated metal (M) which may range, for example, from 0.5/1 to 2/1. This ratio is in most cases of about 1/1.

The first step can be carried out by a reaction in solution, essentially when at least one rare earth metal is to be associated with iron, chromiun, cobalt and/or aluminium. All water soluble compounds of these elements can then be used, in particular their salts of soluble organic or inorganic acids.

The precipitate obtained in convenient conditions (particularly of pH) is first washed; then it may be allowed to mature for a few hours, for example at a temperature of about 60° to 90° C.; it is then filtered and dried at temperatures which may be progressively increased, for example, from 40° to 150° C., and then it is heated at higher temperature ranging, for example, from 400° to 950° C. During this heating step, a mixed oxide of the perovskite type is formed, at least in part.

There can also be operated by reacting together oxides, or species that thermally decompose to oxides, of at least one rare earth metal, on the one hand, and at least one metal M, on the other hand. Particularly, when vanadium is involved, in the form of a compound of vanadium 5+, it is operated under a reducing atmosphere (hydrogen) at a high temperature, for example of from 600° to 900° C. In any case, a calcination is then carried out, at a temperature of from 900° to 1250° C. The resulting product consists at least partly of a mixed oxide of the perorskite type.

In the second step of the process of the invention, the product resulting from the first step is admixed with the other ingredients and with water. The proportions of the iron, chromium, potassium and rare earth metal compounds, calculated as oxides, correspond more particularly to the following ratios by weight:

$\dfrac{Fe_2O_3}{K_2O}$ : from 1/1 to 10/1, preferably from 2/1 to 7/1, $\dfrac{CrO_3}{K_2O}$ : from 0.05/1 to 0.4/1, preferably from 0.1/1 to 0.3/1, and $\dfrac{FeO_3}{CrO_3}$ : from 15/1 to 40/1, preferably from 25/1 to 35/1, the rare earth metal compound, calculated as oxide, representing from 1 to 15%, preferably from 3 to 10% by weight, with respect to the totality of the reactants, calculated as oxides.

When a clayish material is involved, the latter amounts to a proportion of about 3.5 to 30% by weight with respect to the totality of the ingredients involved, calculated as oxides; the potassium compound is used in excess with respect to the amount liable to combine with said clayish material, the potassium excess being, in proportion to iron and chromium, calculated as oxides, in the following ratios by weight:

$\dfrac{Fe_2O_3}{K_2O \text{ excess}}$ : from 3/1 to 10/1; and $\dfrac{CrO_3}{K_2O \text{ excess}}$ : from 0.1/1 to 0.4/1;

The chromium compounds, used alone or as mixtures, are generally chormic anhydride, chromic salts, for example sodium, potassium or ammonium, chromate or bichromate, chromium+3 compounds, for example chromium +3nitrate, sulfate, oxide or hydroxide.

The compounds used for introducing potassium are generally carbonates, oxides and hydroxides. Other salts, such as sulfates, phosphates or nitrates, may also be used.

Examples of clayish materials consist of kaolinite, halloisite, bentonite, montmorillonite, attapulgite or their mixtures. Kaolinite is preferably used, for example as kaolin from Cornouailles.

Finally, a minor proportion of an extrusion aid may be used. Such materials are known in the art and comprise, for example: graphite, vegetal gums (arabic gum, damhar gum, carob gum) or alkylcelluloses(methyl-,ethyl- or carboxymethyl-celluloses).

The catalysts of the invention, prepared as above-described, are used in the dehydrogenation of hydrocarbons, particularly of saturated or monoethylenic aliphatic hydrocarbons and of alkylaromatic hydrocarbons (ethylbenzene, diethylbenzenes), under known-per-se operating conditions as above recalled.

In the dehydrogenation of ethylbenzene to styrene, in particular, the catalysts of the invention provide for a better conversion of ethylbenzene and/or a better selectivity to styrene.

The following examples illustrate the invention but must not be considered in any manner as limiting the scope thereof.

Examples 1,2 and 4 to 9 are given by way of comparison.

EXAMPLE 1

(Catalyst A)

300 g of ferric iron oxide "HA 160", 14.5 g of potassium bichromate, 100 g of anhydrous potassium carbonate and 27 g of lanthanum oxide $La_2O_3$ are malaxed in a WARRING-BLENDER.

The reactants are used in amounts corresponding, as oxides, to the following proportions (% by weight):
$Fe_2O_3 = 73.23\%$
$CrO_3 = 2.41\%$
$K_2O = 17.77\%$
$La_2O_3 = 6.59\%$ The ratios by weight between iron, chromium and potassium, calculated as oxides, are the following:

$\dfrac{Fe_2O_3}{K_2O} = 4.12; \quad \dfrac{CrO_3}{K_2O} = 0.135; \quad \dfrac{Fe_2O_3}{CrO_3} = 30.4$ 67 ml of an aqueous solution at a 2% b.w. concentration of Methocel (sold by DOW CHEMICALS) and 70 ml of water are then added, so as to obtain a firm paste, which is malaxed for 20 minutes and then conveyed to a piston extruder and extruded to elements of 4 mm diameter and 2 to 6 mm length.

The analysis of the final catalyst confirms the contents of iron, chromium, potassium and lanthanum oxides.

EXAMPLE 2

(Catalyst B)

300 g of ferric iron oxide "HA 160", 14.5 g of potassium bichromate, 100 g of anhydrous potassium carbonate, 17.9 of lanthanum oxide $La_2O_3$ and 9.1 g of cobalt oxide $Co_2O_3$ are malaxed in a WARRING-BLENDER apparatus.

The reactants are used in amounts corresponding, as oxides, to the following proportions (in % by weight):
$Fe_2O_3 = 73.23\%$
$CrO_3 = 2.41\%$ $K_2O = 17.77\%$
$La_2O_3 = 4.37\%$
$Co_2O_3 = 2.22\%$ 50 ml of a 2% by weight aqueous solution of Methocel and 100 ml of water are added so as to obtain a paste which is malaxed for 15 minutes and transferred to an extruder. The extrusion, the drying and the activation of the catalyst are effected as above indicated.

EXAMPLE 3

(Catalyst C)

145.5 g of cobalt nitrate and 190 ml of a 2.63 mole/l lanthanum nitrate aqueous solution are poured into 2.5 l of water at 80° C. containing 212 g of $Na_2CO_3$.

The resultant precipitate is washed with 12 liters of distilled water.

After maturation for 6 hours at 80° C., the product is filtered and dried for 24 hours at 50° C., 72 hours at 100° C. and 24 hours at 120° C. A final heating is performed for 2 hours at 600° C.

27 g of the so-obtained product are admixed with 300 g of ferric iron oxide "HA 160", 14.5 g of potassium bichromate and 100 g of anhydrous potassium carbonate.

The reactants are used in amounts corresponding, as oxides, to the following proportions (% by weight):
$Fe_2O_3 = 73.23\%$
$CrO_3 = 2.41\%$
$K_2O = 17.77\%$
$LaCoO_3 = 6.59\%$ The following operations are conducted in the same conditions as above indicated.

EXAMPLE 4

(Catalyst D)

300 g of ferric iron oxide "HA 160", 14.5 g of potassium bichromate, 100 g of anhydrous potassium carbonate, 28.5 g of Cornouailles kaolin and 27 g of lanthanum oxide $La_2O_3$ are malaxed in a WARRING-BLENDER apparatus.

The reactants are used in amounts corresponding, as oxides, to the following percents by weight:
$Fe_2O_3 = 68.47\%$
$CrO_3 = 2.25\%$
$K_2O = 16.62\%$
$La_2O_3 = 6.16\%$
Kaolin $= 6.50\%$ The ratios by weight between iron, chromium and potassium, calculated as oxides, have values close to those indicated in example 1.

The potassium amount liable to combine with kaoline corresponds to a proportion by weight, as oxide, of 2.76% with respect to all the oxides. The proportion of potassium oxide "in excess" is hence 13.86%.

The ratios between iron oxide and chromium oxide, on the one hand, and the $K_2O$ excess, on the other hand, are respectively as follows:

$$\frac{Fe_2O_3}{K_2O \text{ excess}} = 4.94; \quad \frac{CrO_3}{K_2O \text{ excess}} = 0.162$$

67 ml of a 2% by weight Methocel (sold by DOW CHEMICALS) aqueous solution and 70 ml of water are then added, so as to obtain a firm paste.

The operations are then conducted as indicated in example 1.

The analysis of the final catalyst confirms its content of iron, chromium, potassium and lanthanum oxides. The analysis by X-ray diffraction shows the presence of the double aluminium and potassium silicate (kaliophyllite) whose content by weight is 9.3%.

EXAMPLES 5 and 6

(Catalysts E and F)

The preparation of example 4 is repeated, except that, instead of lanthanum oxide $La_2O_3$, the same amount by weight of another rare earth metal oxide is used:
Example 5: cerium oxide $CeO_2$ (catalyst E)
Example 6: neodymium oxide $NdO_3$ (catalyst F)

EXAMPLE 7

(catalyst G)

300 g of ferric iron oxide "HA 160", 14.5 g of potassium bichromate, 100 g of anhydrous potassium carbonate, 28.5 g of Cornouailles kaolin, 17.9 of lanthanum oxide $La_2O_3$ and 9.1 g of cobalt oxide $Co_2O_3$ are malaxed in a WARRING-BLENDER apparatus. The same atomic amounts of lanthanum and cobalt have been selected.

The reactants are used in amounts corresponding, as oxides, to the following proportions: (% by weight):
$Fe_2O_3 = 68.47\%$
$CrO_3 = 2.25\%$
$K_2O = 16.62\%$
$La_2O_3 = 4.08\%$
$Co_2O_3 = 2.08\%$
Kaolin $= 6.50\%$ 50 ml of a 2% by weight Methocel aqueous solution and 100 ml of water are added so as to obtain a paste which is malaxed for 15 minutes. The extrusion, the drying and the calcination of the catalyst are effected as above mentioned.

The content of double aluminium and potassium silicate (kaliophyllite) in the final catalysts is close to 9.3% by weight.

EXAMPLE 8

(catalyst H)

The preparation of example 7 (catalyst G) is repeated except that, instead of cobalt oxide $Co_2O_3$, an equal amount by weight of vanadic anhydride $V_2O_5$ is used.

EXAMPLE 9

(catalyst I)

The preparation of example 7 (catalyst G) is repeated except that, instead of lanthanum oxide $La_2O_3$, the same amount by weight of cerium oxide $CeO_2$ is used and, instead of cobalt oxide $Co_2O_3$, the same amount of vanadic anhydride $V_2O_5$ is used.

EXAMPLE 10

(catalyst J)

145.5 g of cobalt nitrate and 190 ml of a 2.63 mole/l lanthanum nitrate aqueous solution are poured into 2.5 l of water at 80° C. containing 212 g of $Na_2CO_3$. The reactants are used in amounts corresponding to an atomic ratio of cobalt to lanthanum of 1/1.

The resultant precipitate is washed with 12 liters of distilled water. After maturation for 6 hours at 80° C., the product is filtered and dried for 24 hours at 50° C., 72 hours at 100° C. and then 24 hours at 120° C. Finally, heating is preformed for 2 hours at 600° C.

The structure of the resultant product was not identified with certainty. It seems that it consists, at least partially, of a mixed oxide of the perovskite type LaCoO$_3$.

27 g of the so-prepared product is admixed with 300 g of ferric iron oxide "HA 160", 14.5 g of potassium bichromate, 100 g of anhydrous potassium carbonate and 28.5 g of Cornouailles kaolin.

The reactants are used in amounts corresponding, as oxides, to the following proportions (% by weight):
Fe$_2$O$_3$ = 68.47%
CrO$_3$ = 2.25%
K$_2$O = 16.62%
LaCoO$_3$ = 6.16%
Kaolin = 6.50%

The following operations are performed in the same conditions as above mentioned.

EXAMPLE 11

(Catalyst K)

163 g of lanthanum oxide La$_2$O$_3$ and 91 g of vanadic anhydride V$_2$O$_5$ are reacted in the solid state by mixing under a hydrogen atmosphere at 850° C. for 6 Hours. The mixture is then calcined for 18 hours at 1200° C. The oxides are used in proportions corresponding to an atomic ratio La/V of about 1/1.

The product obtained consists at least partly of a mixed oxide LaVO$_3$ of the perovskite type.

It is then proceeded as described in example 10.

EXAMPLE 12

(Catalyst L)

The preparation described in example 11 (catalyst K) is repeated, except that lanthanum oxide La$_2$O$_3$ is replaced by cerium oxide CeO$_2$, in an amount corresponding to an atomic ratio Ce/V of about 1/1.

The resulting product consists, at least in part, of a mixed oxide CeVO$_3$ of the perovskite type.

It is then proceeded in the same manner as described in example 10.

EXAMPLES 13 to 18

(catalysts M to R)

Salts of rare earth metals (RE) and salts of other metals (M) in amounts corresponding to an atomic ratio RE/M of about 1/1 are reacted in water solution. The procedure is then continued as indicated in example 10.

The resultant products may be represented by the formulas of Table 1.

TABLE 1

| EXAMPLE N° | CATALYST | MIXED OXIDE |
| --- | --- | --- |
| 13 | M | LaCrO$_3$ |
| 14 | N | LaFeO$_3$ |
| 15 | O | LaCr$_{0.6}$Fe$_{0.4}$O$_3$ |
| 16 | P | CeCrO$_3$ |
| 17 | Q | CeFeO$_3$ |
| 18 | R | NdCrO$_3$ |

The other steps of the preparation are identical to those described in example 10.

The analysis of the catalysts obtained as described in examples 1 to 18, indicates that their percent composition, as oxides, is close to the composition of the constituents used for their preparation as concerns iron, chromium, potassium, rare earth metals (RE) and, optionally, the associated metal (M).

Moreover, with respect to examples 4 to 18, the analysis by X-ray diffraction, detects a content of double aluminium and potassium silicate of about 9.3% by weight.

The catalysts A to R were subjected to a long run catalyst test.

The catalyst test is effected in a "catatest" operated under atmospheric pressure and fed with ethylbenzene of industrial grade and water. The tested catalyst volume is 100 ml (60 to 120 g of catalyst).

The catalysts A to R are shaped as extrudates of a 4 mm diameter and a 4–5 mm length.

The catalyst is first preheated up to about 500° C. Steam is then introduced and, at about 550° C., ethylbenzene is introduced. The temperatures are then adjusted so as to obtain a temperature of 614±2° C. within the catalyst bed.

The selected hourly flow rates are as follows:

$$\frac{\text{Ethylbenzene}}{\text{Catalyst}} = 0.4 \text{ volume } v^{-1} h^{-1}; \quad \frac{\text{H}_2\text{O}}{\text{Ethylbenzene}} = 2 \text{ g g}^{-1}$$

Table 2 indicates the conversion of ethylbenzene ($C_{EB}$), the selectivity to styrene ($S_{ST}$) and the styrene yield ($Y_{ST}$); these figures are expressed in mole % and correspond to the following definitions:

$$C_{EB} = \frac{\text{moles of converted ethylbenzene}}{\text{moles of supplied ethylbenzene}} \times 100$$

$$S_{ST} = \frac{\text{moles of ethylbenzene converted to styrene}}{\text{moles of converted ethylbenzene}} \times 100$$

$$Y_{ST} = \frac{\text{moles of produced styrene}}{\text{moles of supplied ethylbenzene}} \times 100$$

These values are linked by the relationship:

$$Y_{ST} = C_{EB} \times S_{ST} \times 1/100$$

The performances of the catalysts are summarized in table 2.

In this table, the comparison between example 3 and example 2, the comparison between examples 13, 14 and 15 and example 4, the comparison between example 10 and example 7, the comparison between example 11 and example 8, the comparison between example 16 and 17 and example 5, the comparison between example 18 and example 6, and the comparison between example 12 and example 9 show that the mode of preparation according to the invention, comprising the preliminary step of formation of an association of a rare earth metal oxide with another metal (M) oxide (with intermediate calcination), confers improved properties to the catalysts as compared with the catalysts obtained when all the metals are introduced in a single step.

TABLE 2

| Catalyst | A | B | C | D | E | F | G | H | I | J | K | L | M | N | O | P | Q | R |
| --- | --- | --- | --- | --- | --- | --- | --- | --- | --- | --- | --- | --- | --- | --- | --- | --- | --- | --- |
| Example | 1 | 2 | 3 | 4 | 5 | 6 | 7 | 8 | 9 | 10 | 11 | 12 | 13 | 14 | 15 | 16 | 17 | 18 |
| Convers. EB % mol. | 59.9 | 60.8 | 65.8 | 60.0 | 60.2 | 59.0 | 61.0 | 60.0 | 60.1 | 65.9 | 61.0 | 60.5 | 65.4 | 62.5 | 62.0 | 65.5 | 62.1 | 61.9 |
| Select. ST | 92.0 | 90.5 | 91.7 | 92.1 | 90.0 | 92.5 | 90.5 | 92.5 | 90.5 | 91.9 | 92.0 | 90.4 | 91.5 | 92.7 | 92.8 | 90.4 | 92.6 | 90.3 |

TABLE 2-continued

| Catalyst | A | B | C | D | E | F | G | H | I | J | K | L | M | N | O | P | Q | R |
|---|---|---|---|---|---|---|---|---|---|---|---|---|---|---|---|---|---|---|
| Example | 1 | 2 | 3 | 4 | 5 | 6 | 7 | 8 | 9 | 10 | 11 | 12 | 13 | 14 | 15 | 16 | 17 | 18 |
| % mol. Yield ST % mol. | 55.1 | 56.2 | 60.3 | 55.3 | 54.2 | 54.6 | 55.2 | 55.5 | 54.4 | 60.5 | 56.1 | 54.7 | 59.8 | 57.9 | 57.5 | 59.2 | 57.2 | 55.9 |

EXAMPLES 19 to 32

In the same manner as for examples 10 to 18, various other oxide combinations have been prepared with, on the one hand, at least one rare earth metal and, on the other hand, at least one metal M selected from iron, chromium, cobalt, aluminum and vanadium. The oxides combinations may be considered, at least partly, as similar to mixed oxides of the perovskite type complying with the formulas given in Table 3 below.

TABLE 3

| EXAMPLE N° | CATALYST | MIXED OXIDE |
|---|---|---|
| 19 | S | $LaAlO_3$ |
| 20 | T | $La_{0.5}Pr_{0.5}CoO_3$ |
| 21 | U | $La_{0.7}Nd_{0.3}Fe_{0.5}Co_{0.5}O_3$ |
| 22 | V | $PrAlO_3$ |
| 23 | W | $PrCo_{0.1}Fe_{0.9}O_3$ |
| 24* | X | $Pr_{0.8}Sc_{0.2}VO_3$ |
| 25 | Y | $NdAl_{0.3}Co_{0.7}O_3$ |
| 26 | Z | $SmFeO_3$ |
| 27 | AA | $SmCr_{0.8}Co_{0.2}O_3$ |
| 28 | AB | $EuCrO_3$ |
| 29 | AC | $GdCoO_3$ |
| 30* | AD | $GdFe_{0.5}V_{0.5}O_3$ |
| 31 | AE | $DyAlO_3$ |
| 32 | AF | $YbCr_{0.4}Fe_{0.4}Co_{0.2}O_3$ |

*In examples 24 and 30, it was operated in the same manner as in example 11.

The next preparation steps are identical to those described in example 10.

The so-formed catalysts have been tested in the above-mentioned conditions. Their performances are summarized in Table 4. The styrene yields are particularly high.

TABLE 4

| Catalyst | S | T | U | V | W | X | Y |
|---|---|---|---|---|---|---|---|
| Example | 19 | 20 | 21 | 22 | 23 | 24 | 25 |
| Convers. EB % mol. | 64.0 | 63.7 | 62.0 | 65.4 | 61.8 | 62.2 | 62.0 |
| Select. ST % mol. | 90.6 | 92.1 | 90.5 | 91.9 | 93.4 | 92.1 | 92.2 |
| Yield ST % mol. | 58.0 | 58.7 | 56.1 | 60.1 | 57.7 | 57.3 | 57.2 |

| Catalyst | Z | AA | AB | AC | AD | AE | AF |
|---|---|---|---|---|---|---|---|
| Example | 26 | 27 | 28 | 29 | 30 | 31 | 32 |
| Convers. EB % mol. | 64.0 | 65.8 | 64.1 | 62.2 | 62.3 | 67.2 | 65.5 |
| Select. ST % mol. | 91.9 | 91.2 | 90.8 | 92.2 | 92.1 | 90.8 | 93.2 |
| Yield ST % mol. | 58.8 | 60.0 | 58.2 | 57.3 | 57.4 | 61.0 | 61.0 |

What is claimed as the invention is:

1. A process for manufacturing a catalyst containing iron, chromium and potassium, as oxides, in the ratios by weight:

$$\frac{Fe_2O_3}{K_2O} \text{ from 1/1 to 10/1}$$

$$\frac{CrO_3}{K_2O} \text{ from 0.05/1 to 0.4/1}$$

$$\frac{Fe_2O_3}{CrO_3} \text{ from 15/1 to 40/1,}$$

and at least one rare earth metal, in a proportion, calculated as oxide, from 1 to 15% by weight with respect to the weight of said catalyst, said process being characterized in that it comprises:

a first step of manufacturing a product by reacting at least one rare earth (RE) metal compound with at least one compound of at least one metal (M) selected from iron, chromium, cobalt, aluminium and vanadium, said reaction being followed with heating at high temperature; and a second step of forming a mixture comprising water, at least one iron compound, at least one chromium compound, at least one potassium compound and the product obtained at the end of the first step, the various metal compounds being used in proportions corresponding to the indicated oxide proportions by weight, malaxing said mixture to form a paste which is then dried and thermally activating the catalyst by heating at high temperature.

2. A process according to claim 1, characterized in that, in the catalyst, the ratios by weight between iron, chromium and potassium, calculated as oxides, are:

$$\frac{Fe_2O_3}{K_2O} \text{ from 2/1 to 7/1}$$

$$\frac{CrO_3}{K_2O} \text{ from 0.1/1 to 0.3/1; and}$$

$$\frac{Fe_2O_3}{CrO_3} \text{ from 25/1 to 35/1,}$$

and the proportion of rare earth metal, calculated as oxide, is from 3 to 10% by weight.

3. A process according to claim 2, characterized in that the rare earth metal is lanthanum, praseodymium or neodymium.

4. A process according to one of claims 1 or 2, characterized in that the rare earth (RE) metal and metal (M) compounds are used in proportions corresponding to an atomic ratio RE/M of from about 0.5/1 to 2/1.

5. A process according to claim 4, characterized in that said atomic ratio RE/M is about 1/1.

6. A process according to one of claims 1 or 2, characterized in that, in the first step, the reaction is carried out in solution between at least a soluble compound of a rare earth metal and at least a soluble compound of iron, chromium, cobalt or aluminium, the resulting precipitate is separated, dried, and heated at a temperature of from 400° to 950° C.

7. A process according to one of claims 1 or 2, characterized in that in the first step the reaction is carried out between oxides or species that thermally decompose to oxides, of said at least one rare earth metal, RE, and said at least one metal M, under heating a temperature of from 900° to 1250° C.

8. A process according to one of claims 1 or 2, characterized in that, in the first step, there is operated by mixing oxides, or species that thermally decompose to oxides, of at least one rare earth metal, on the one hand, and vanadium, on the other hand, under a reducing atmosphere and at a temperature of from 600° to 900° C., and the mixture obtained is calcined at a temperature of from 900° to 1250° C.

9. A process according to one of claims 1 or 2, characterized in that the product obtained at the end of the first step is comprised of, at least partly, a mixed oxide of the perovskite type.

10. A process according to one of claims 1 or 2, characterized in that, during the second step, a clayish material is used in a proportion from 3.5 to 30% by weight with respect to the totality of the mixture components, calculated as oxides, the potassium compound being used in excess with respect to the amount liable to combine with said clayish material to form a double aluminium and potassium silicate, the excess of said potassium compound being, in proportion to iron and chromium, calculated as oxides, in the following ratios by weight:

$$\frac{Fe_2O_3}{K_2O \text{ excess}} : \text{from } 3/1 \text{ to } 10/1; \text{ and}$$

$$\frac{CrO_3}{K_2O \text{ excess}} : \text{from } 0.1/1 \text{ to } 0.4/1$$

11. A process according to claim 10, characterized in that said clayish material is comprised of at least partly of kaolinite.

12. A process according to claim 1, characterized in that the thermal activation of the catalyst at the end of the second step is effected at a temperature from 850° to 1100° C.

13. A catalyst prepared by the process of claim 1.

14. In a process for manufacturing a catalyst containing iron, chromium and potassium, as oxides, in the ratios by weight:

$$\frac{Fe_2O_3}{K_2O} \text{ from } 1/1 \text{ to } 10/1$$

$$\frac{CrO_3}{K_2O} \text{ from } 0.05/1 \text{ to } 0.4/1$$

$$\frac{Fe_2O_3}{CrO_3} \text{ from } 15/1 \text{ to } 40/1$$

and at least one rare earth metal, in a proportion, calculated as oxide, from 1 to 15% by weight with respect to the weight of said catalyst, said process being characterized in that is comprises:

a step of forming a mixture comprising water, at least one iron compound, at least one chromium compound, at least one potassium compound, and a product obtained by reacting at least one rare earth (RE) metal compound with at least one compound of at least one metal (M) selected from iron, chromium, cobalt, aluminium and vanadium, said reaction being followed with heating at high temperature, and the various metal compounds being used in proportions corresponding to the indicated oxide proportions by weight, malaxing said mixture to form a paste, and then drying said paste.

15. A process according to claim 14, characterized in that, in the catalyst, the ratios by weight between iron, chromium and potassium, calculated as oxides, are:

$$\frac{Fe_2O_3}{K_2O} \text{ from } 2/1 \text{ to } 7/1$$

$$\frac{CrO_3}{K_2O} \text{ from } 0.1/1 \text{ to } 0.3/1$$

$$\frac{Fe_2O_3}{CrO_3} \text{ from } 25/1 \text{ to } 35/1$$

and the proportion of rare earth metal, calculated as oxide, is from 3 to 10% by weight.

16. A process according to claim 14, wherein said product is obtained by conducting the reaction in solution between at least a soluble compound of a rare earth metal and at least a soluble compound of iron, chromium, cobalt or aluminum, the resulting precipitate is separated, dried, and heated at a temperature of from 400° to 950° C.

17. A process according to claim 14, wherein said reacting is conducted between oxides or species that thermally decompose to oxides, of said at least one rare earth metal, RE, and said at least one metal M, under heating a temperature of from 900° to 1250° C.

18. A non-activated catalyst as produced by the process of claim 14.

19. A process according to claim 13, further comprising thermally activating the catalyst by heating at a temperature of 850°–1100° C.

20. A catalyst as produced by the process of claim 19.

* * * * *